(12) United States Patent
Ko

(10) Patent No.: US 7,101,518 B1
(45) Date of Patent: Sep. 5, 2006

(54) PLASMA DISINFECTION SYSTEM

(75) Inventor: Jung Suek Ko, Seoul (KR)

(73) Assignee: Human Meditek Co., LTD, Seoul (KR)

( * ) Notice: Subject to any disclaimer, the term of this patent is extended or adjusted under 35 U.S.C. 154(b) by 0 days.

(21) Appl. No.: 10/239,496

(22) PCT Filed: May 26, 2000

(86) PCT No.: PCT/KR00/00539

§ 371 (c)(1),
(2), (4) Date: Sep. 20, 2002

(87) PCT Pub. No.: WO01/70281

PCT Pub. Date: Sep. 27, 2001

(30) Foreign Application Priority Data

Mar. 23, 2000 (KR) ............................... 2000-14750

(51) Int. Cl.
*A61L 9/00* (2006.01)

(52) U.S. Cl. .................. 422/305; 222/41; 222/305; 222/309; 222/333; 422/298; 422/306

(58) Field of Classification Search ............... 222/333, 222/52, 309, 41; 422/23, 22, 29, 305, 298, 422/306
See application file for complete search history.

(56) References Cited

U.S. PATENT DOCUMENTS

| | | | | |
|---|---|---|---|---|
| 3,526,481 A | * | 9/1970 | Rubricius | ..................... 422/48 |
| 3,901,408 A | * | 8/1975 | Boden et al. | .................. 422/28 |
| 4,756,882 A | | 7/1988 | Jacobs et al. | |
| 5,667,105 A | * | 9/1997 | Hartley et al. | ............... 222/148 |
| 5,772,899 A | * | 6/1998 | Snodgrass et al. | .......... 210/767 |
| 6,077,480 A | * | 6/2000 | Edwards et al. | ............... 422/28 |

OTHER PUBLICATIONS

International Search Report - PCT/KR00/00539, ISA/KR, Dec. 27, 2000.

* cited by examiner

*Primary Examiner*—Krisanne Jastrzab
(74) *Attorney, Agent, or Firm*—Harness, Dickey & Pierce

(57) ABSTRACT

Disclosed is an apparatus for supplying liquid for use in a plasma disinfection system. The apparatus supplies liquid for generating plasma to a reaction chamber (1) to sterilize and disinfect an item wrapped in a packaging material (10) in the reaction chamber (1). The apparatus includes: an automatic feeder (20) for automatically feeding an extremely small fixed amount of liquid via a first discharging pipe (40) by controlling a rotational speed of a DC motor (31); a vaporizer (24) connected to the first discharging pipe (40) of the automatic feeder (20) and having a first heater (26) for vaporizing the fed liquid; a second heater (22) surrounding a second discharging pipe (23) connected between the vaporizer (24) and the reaction chamber (1) to prevent any condensation of the vaporized liquid in the second discharging pipe (23); and a temperature controller (25) electrically connected to the first and second heaters (26 and 22) to control temperatures thereof.

1 Claim, 2 Drawing Sheets

PLASMA DISINFECTION SYSTEM

TECHNICAL FIELD

The present invention relates to an apparatus for supplying liquid for use in a plasma disinfection system for sterilizing and disinfecting surfaces of objects such as medical instruments with gaseous plasma, and, more particularly, to an apparatus for supplying liquid which is capable of automatically supplying liquid for generating plasma, i.e., hydrogen peroxide, in increments of a fixed small amount.

BACKGROUND ART

Various methods of sterilization and disinfection have been used for the sterilization of different types of disposable and reusable medical equipment. Among these methods, a method of sterilization and disinfection by steam or by dry heat has been used extensively used. However, this method of sterilization and disinfection cannot be applied to sterilize materials that are adversely affected by such heat or steam.

Ethylene oxide (EtO) gas has also been used but suffers from the drawback that it may leave toxic residues on the articles to be sterilized, which may have adverse effects on patients who come into contact with such articles. Consequently, with this method, an additional procedure required to remove residual ethylene oxide from some sterilized items also causes the ethylene oxide sterilization procedure to be high in cost and to take a long in time.

Among methods for overcoming the aforesaid drawbacks, there is a method using hydrogen peroxide as a precursor of active species in a low temperature plasma system. This method is generally carried out in such a way that an object to be sterilized and disinfected is first brought in to contact with gaseous hydrogen peroxide as a pre-treatment, and the object is finally sterilized and disinfected by hydrogen peroxide plasma generated by supply of a required amount of electric power, so as to reduce a length of time required to sterilize and disinfect by plasma.

In the above low temperature plasma disinfection system, an apparatus for supplying hydrogen peroxide employs a capsule type cassette system containing a certain amount of hydrogen peroxide solution. The hydrogen peroxide solution contained in the capsule is fed to a solution-feeding pipe by means of an injection pump, and the fed hydrogen peroxide solution in a liquid phase is vaporized by a vaporizer, which is then fed into a sterilization reactor.

With the above capsule type cassette system, however, a used cassette must be replaced by a new one with ten capsules in it after the sterilization process is carried out ten times since one capsule is used in one sterilization process. In addition, the above vaporizer has drawbacks that the above apparatus for supplying an extremely small fixed amount of liquid is very complicated and very expensive.

DISCLOSURE OF THE INVENTION

Accordingly, the present invention has been made keeping in mind the above problems occurring in the prior art, and an object of the present invention is to provide an apparatus for supplying liquid for generating plasma, which is intended to avoid inconvenience caused by frequent replacement of cassettes in the capsule type cassette system and to reduce its manufacturing cost by simplification of its configuration, and which is also intended to automatically supply hydrogen peroxide liquid for generating plasma in increments of a fixed small amount.

In order to accomplish the above object, the present invention provides an apparatus for supplying liquid for generating plasma to a reaction chamber to sterilize and disinfect an item wrapped in a packaging material in the reaction chamber, comprising: an automatic feeder for automatically feeding an extremely small fixed amount of liquid for generating plasma via a first discharging pipe by controlling a rotational speed of a DC motor; a vaporizer connected to the first discharging pipe of the automatic feeder and having a first heater for vaporizing the fed liquid; a second heater surrounding a second discharging pipe connected between the vaporizer and the reaction chamber to prevent any condensation of the vaporized liquid in the second discharging pipe; and a temperature controller electrically connected to the first and second heaters to control temperatures thereof.

The automatic feeder may comprise: a DC motor having a retarder, of which a speed is feed-back controlled by a proportional control circuit; a feeding screw connected to a rotating shaft of the DC motor; a supporting member engaged with the feeding screw to be moved back and forth along the feeding screw by rotation of the feeding screw; an injection piston coupled to the supporting member to be linearly moved together with the supporting member; an injection cylinder supported by two fixing plates and receiving the injection piston, the injection cylinder being provided with a feeding valve adapted to be opened at the time of retraction of the injection piston and an exhaust valve adapted to be opened at the time of extension of the injection piston; a liquid supplying container connected to the feeding valve of the injection cylinder for supplying liquid for generating plasma to the injection cylinder; and a displacement sensor provided at the fixing plate to detect a position of the injection piston.

BRIEF DESCRIPTION OF THE DRAWINGS

The above and other objects, features and advantages of the present invention will be more clearly understood from the following detailed description taken in conjunction with the accompanying drawings, in which.

BEST MODE FOR CARRYING OUT THE INVENTION

Figure 1:
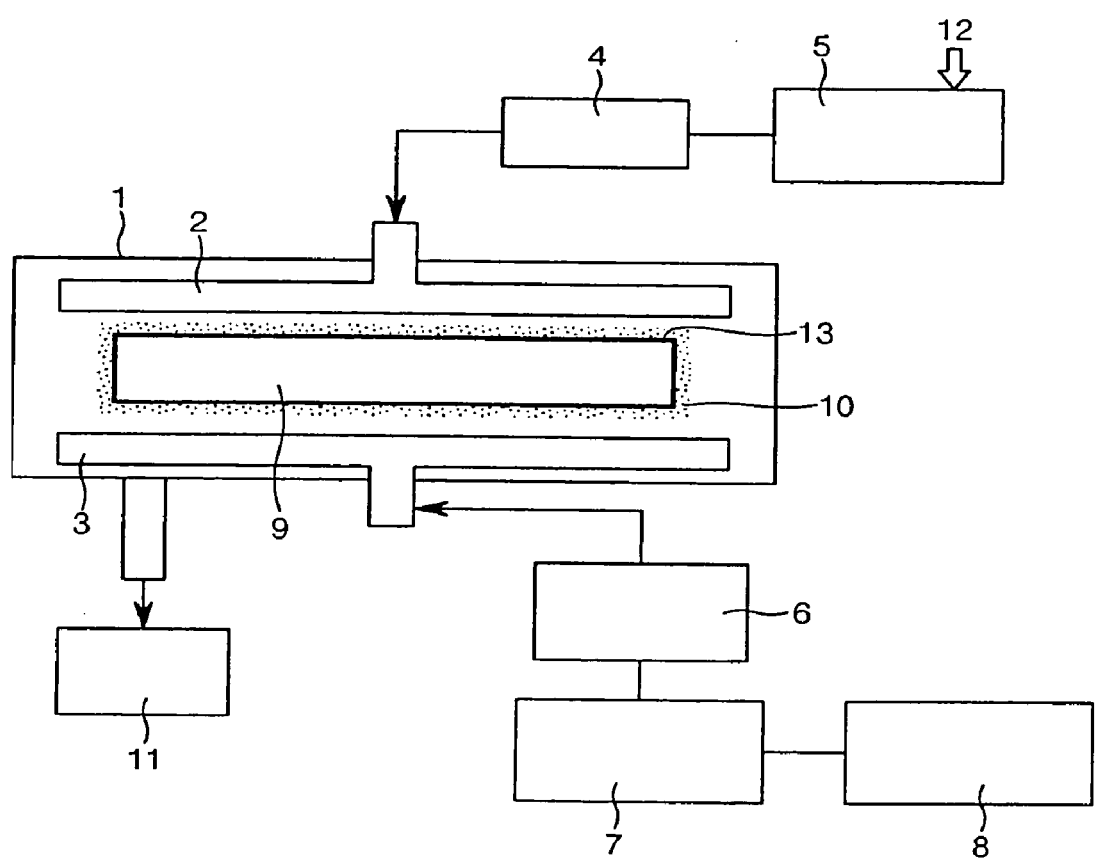
FIG. 1 is a schematic view of a plasma sterilization system to which an apparatus for supplying liquid according to the present invention is applied.

Reference now should be made to the drawings, in which the same reference numerals are used throughout the different drawings to designate the same or similar components.

FIG. 1 is a schematic view of a plasma sterilization system to which an apparatus for supplying liquid according to the present invention is applied, which is a system for sterilizing and disinfecting an item in a gaseous plasma.

The plasma sterilization system uses a hydrogen peroxide solution 12 as a source for generation of the plasma to sterilize and disinfect surfaces of an item 9 to be sterilized such as medical instruments, and also uses hydrogen peroxide as an active species during generation of the plasma. Prior to the generation of the plasma (which is generated by electric discharge of gas), a pre-treatment is carried out with gaseous plasma.

A reaction chamber 1 receives an item 9 to be sterilized such as medical or surgical instruments, which is wrapped in a packaging material 10. The reaction chamber 1 is provided at its inner and upper position with an anode 2 and at its inner and lower position with a cathode 3. The anode 2 is connected to a mass flow controller 4, which is in result connected to an injection heater 5. The cathode 3 is connected to an impedance matching circuit 6, which is in result connected to a plasma power source 8 through an impedance matching controller 7. Furthermore, disposed below the reaction chamber 1 is a vacuum pump 11, which serves to draw out air of the reaction chamber 1.

In the plasma sterilization system according to the present invention, after the item 9 to be sterilized, such as medical or surgical instruments, which is wrapped in the packaging material 10, is placed in the reaction chamber 1, the reaction chamber 1 is closed, and air is drawn out of the reaction chamber 1 by means of the vacuum pump 11 to form a vacuum inside of the reaction chamber 1. At this point, the hydrogen peroxide solution 12 in a liquid phase is turned into gaseous hydrogen peroxide by means of the injection heater 5, and the gaseous hydrogen peroxide is adjusted to a predetermined pressure (approximately 0.1–10 Torr) by means of the mass flow controller 4 and then injected into the anode 2. The hydrogen peroxide remains in the chamber for a predetermined time period (approximately 30 minutes) to allow extensive contact between the hydrogen peroxide and the item 9 to be sterilized.

After the electric power is set to a desired level using the plasma power source 8, the power is adjusted by the impedance matching controller 7 so that a level corresponds to a resistance value of the gaseous hydrogen peroxide in the reaction chamber 1, and then reaches the cathode 3 through the impedance matching circuit 6, thereby supplying the optimal power to the cathode 3. By the supply of the power to the cathode 3, plasma is generated between the cathode 3 and the anode 2.

The plasma remains in the reaction chamber 1 for a sufficient time (approximately 50 minutes) to allow complete sterilization, although the sterilization can be effected in periods as short as 5 minutes from initial plasma generation, depending on the plasma power source 8 that is applied to the cathode 3 and a concentration of the hydrogen peroxide.

Therefore, it is preferable to apply the optimal power in order to obtain the optimal efficiency of sterilization since the efficiency of sterilization relies on the plasma power source 8 as well as the concentration of hydrogen peroxide.

Since the packaging material 10 is used to wrap the item 9 to be sterilized, and is then placed in the reaction chamber 10, the preferred material of the packaging material is a fibriform polyethylene or polyethylene terephthalate to have favorable gas permeability. Alternatively, although the packaging material 10 may be a paper to reduce manufacturing costs, longer processing times may be required to achieve complete sterilization because of possible interactions of hydrogen peroxide and other reactive species with the paper.

In the plasma sterilization system according to the present invention, a pressure of gaseous hydrogen peroxide as reaction gas is set to less than 10 Torr, and a high-frequency (RF 13.56 MHz) capacity combination type, in which the high-frequency power is intermittently applied in the form of pulse, is used to generate plasma with a temperature of less than 100° C.

In the present invention, the reason why the intermittent application of high-frequency power is employed is that the intermittent application prevents overheating of the reaction gas in the reaction chamber 1 as well as overheating of the item 9 to be sterilized. The intermittent application of power is carried out in such a way that high-frequency power is applied for 0.5 ms and then turned off for 1 ms prior to re-application.

As described above, hydrogen peroxide is injected into the anode 2 of the reaction chamber 1 in order to carry out the pre-treatment. At this point, preferably a concentration of the gaseous hydrogen peroxide is 0.05 to 10 mg/liter, but a higher concentration of hydrogen peroxide will result in shorter sterilization times since efficiency of the sterilization becomes higher.

The minimum concentration of hydrogen peroxide injected into the reaction chamber 1 is approximately 0.125 mg/liter. When the hydrogen peroxide is injected at an appropriate concentration, auxiliary gases such as oxygen, nitrogen, argon or the like may be added into the reaction chamber.

When an item 9 to be sterilized such as medical or surgical instruments is sterilized by the present invention, no additional steps are required to remove residual hydrogen peroxide from the sterilized item 9 or its packaging material 10, since the hydrogen peroxide is decomposed into non-toxic products during the plasma treatment, unlike a conventional ethylene oxide process, which is a conventional gas sterilization process.

Figure 2:
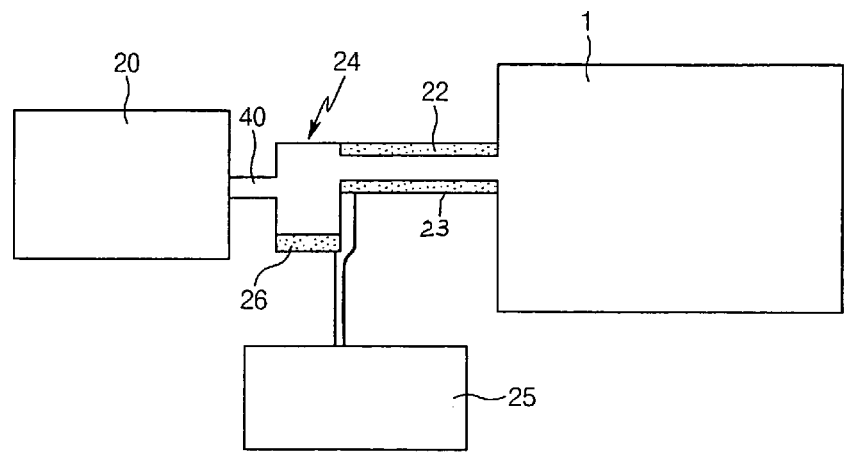
FIG. 2 is a schematic view of the apparatus for supplying liquid, which is an essential part of the present invention.

FIG. 2 is a schematic view of the apparatus for supplying liquid, which is an essential part of the present invention.

The apparatus for supplying liquid is designed to cause liquid for generating plasma supplied from an automatic feeder 20 to be vaporized at a vaporizer 24 disposed between a fist discharging pipe 40 and a second discharging pipe 23 and then to be supplied to an reaction chamber 1. The automatic feeder 20 is adapted to automatically supply an extremely small fixed amount of liquid for generating plasma to the first discharging pipe 40 by a DC motor 31. The first discharging pipe 40 is connected at its end to the vaporizer 24, which vaporizes the liquid supplied through the first discharging pipe 40 by a first heater 26. The second discharging pipe 23 connected to the vaporizer 24 is provided at its outer surface with a second heater 22 to prevent condensation of the vaporized liquid supplied to the reaction chamber 1. Temperatures of the first and second heaters 26 and 22 are controlled by a temperature controller 25, which is electrically connected thereto.

Figure 3:
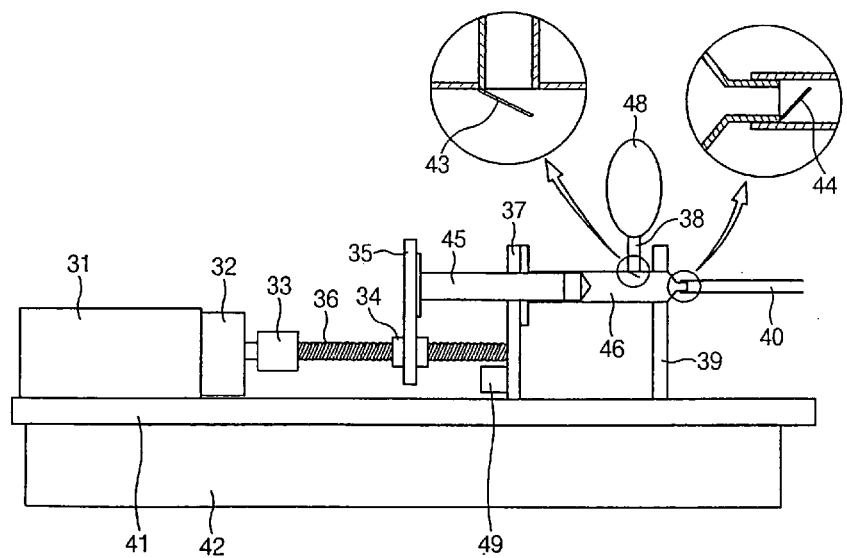
FIG. 3 is a schematic view of an automatic feeder of FIG. 2.

As shown in FIG. 3, the automatic feeder 20 causes an injection piston 45 connected to the DC motor 31, of which a speed is feed-back controlled by a proportional control circuit 12 of the controller, to be linearly moved at a desired speed. Consequently, it is possible to control amount of liquid supplied per unit time, which is determined from a cross section of the injection piston 45 and a displacement volume per unit time by driving of the injection piston. After the liquid whose volume corresponds to that of an injection cylinder 46 is depleted, the DC motor 31 is reversely rotated to cause the injection piston 45 to be retracted, thereby allowing the liquid in a liquid supplying container 48 to be automatically injected into the injection cylinder 46.

The automatic feeder 20 will now be described in more detail. The DC motor 31 is feed-back controlled by the proportional control circuit 42, and includes a retarder 32. A rotating shaft of the DC motor 31 is connected to a feeding screw 36 by a coupling 33, such that the feeding screw 36 is rotated in a state of being aligned with the rotating shaft. An end of the feeding screw 36 is supported by a fixing plate 37.

The feeding screw 36 is provided thereon with a supporting member 35 via a feeding nut 34 so that the supporting member 35 is moved back and forth along the feeding screw 36 by rotation of the feeding screw 36. The supporting member 35 is connected to the injection piston 45, which is linearly moved along an axis parallel to the feeding screw 36. The injection piston 45 is air-tightly received in an injection cylinder 46, which accommodates the linear movement of the injection piston 45, and is supported by two fixing plates 37 and 39. The injection cylinder 46 is provided with a feeding valve 43 adapted to be opened at the time of retraction of the injection piston 45 and an exhaust valve 44 adapted to be opened at the time of extension of the injection piston 45, so as not to hinder the linear movement of the injection piston 45.

The injection cylinder 46 is communicated with the liquid supplying container 48 for storing liquid for generating plasma, which is provided with the feeding valve 43 at its lower end. The fixing plate 37 is provided with a displacement sensor 49 for detecting a position of the injection piston 45. The DC motor 31 and the fixing plates 37 and 39 are fixedly mounted on a mounting member 41.

A process for automatically supplying an extremely small fixed amount of hydrogen peroxide solution to the reaction chamber 1 using the apparatus for supplying liquid according to the present invention will now be described.

After liquid for generating plasma is first filled in the injection cylinder 46, the DC motor 31 is activated by the proportional control circuit 42. Consequently, the feeding screw 36 connected to the rotating shaft of the DC motor 31 is rotated, thereby causing the supporting member 35 engaged therewith to be linearly advanced along the feeding screw 36.

When the supporting member 35 is moved forwardly, the injection piston 45 coupled to the supporting member 35 is also moved forwardly, so that an amount of liquid in the injection cylinder 46 corresponding to a distance by which the injection cylinder is moved, is discharged.

Thereafter, the DC motor 31 is controlled by the proportional control circuit 42 to advance the injection piston 45 at a desired velocity. By this advance of the injection piston 45, the liquid in the injection cylinder 46 is automatically supplied in increments of a fixed small amount. In this case, an amount of the supplied liquid can be derived from a transfer distance per unit time of the injection piston 45 and a cross section of the inside of the injection cylinder 46. From the transfer distance per unit time of the injection piston 45, a rotational velocity of the DC motor 31 can be derived, so that a time period required to supply a predetermined small amount of liquid can be calculated. Accordingly, the liquid in the injection cylinder 46 is automatically supplied in increments of a fixed small amount. At this point, the feeding valve 43 of the injection cylinder 46 is closed while the exhaust valve 44 is opened.

The liquid discharged from the exhaust valve 44 of the injection cylinder 46 is vaporized by the first heater 26 mounted on the vaporizer 24, and then injected into the reaction chamber 1 through the second discharging pipe 23. In the present invention, since the second discharging pipe 23 connected to the vaporizer 24 is fully covered with the second heater 22, the liquid flowing in the second discharging pipe 23 can be maintained in a vaporized state, and there is no temperature difference between the inside of the pipe and the outside of the pipe. Temperatures of the first and second heater 26 and 22 are constantly controlled by the temperature control circuit 25.

By generating plasma from the vaporized liquid supplied to the reaction chamber 1, the plasma sterilization process is carried out.

As the injection piston 45 continues to advance, the injection piston 45 is detected by the displacement sensor 49 provided at the fixing plate 37 supporting the injection cylinder 46. When the injection piston 45 is completely moved forwardly until depletion of the liquid in the injection cylinder 46, the injection piston 45, i.e., the depletion of the liquid is detected by the displacement sensor 49. By a signal from the displacement sensor, the DC motor 31 is rotated reversely to cause the injection piston 45 to be retracted, so that the liquid in the liquid supplying container 48 is filled in the injection cylinder 46 through a liquid supplying pipe 38. At this point, the exhaust valve 44 of the injection cylinder 46 is closed while the feeding valve 43 is opened.

INDUSTRIAL APPLICABILITY

As described above, the present invention provides an apparatus for supplying liquid for use in a plasma disinfection system used in hospitals, which is capable of supplying an extremely small amount of liquid to a sterilization and disinfection chamber or a reaction chamber. The apparatus for supplying liquid according to the present invention enables its configuration to be simplified and its manufacturing cost to be lowered, and can be used for a long time with only one filling procedure of liquid without frequent replacement of a cassette containing liquid.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. An apparatus for supplying liquid for generating plasma to a reaction chamber (1) to sterilize and disinfect an item wrapped in a packaging material (10) in the reaction chamber (1), comprising:
   an automatic feeder (20) for automatically feeding a fixed amount of liquid for generating plasma via a first discharging pipe (40) by controlling a rotational speed of a DC motor (31);
   a vaporizer (24) connected to the first discharging pipe (40) of the automatic feeder (20) and having a first heater (26) for vaporizing the fed liquid;
   a second heater (22) surrounding a second discharging pipe (23) connected between the vaporizer (24) and the reaction chamber (1) to prevent any condensation of the vaporized liquid in the second discharging pipe (23); and
   a temperature controller (25) electrically connected to the first and second heaters (26 and 22) to control temperatures thereof; and wherein the automatic feeder (20) comprises:
   a DC motor (31) having a retarder (32) of which a speed is feed-back controlled by a proportional control circuit (42);
   a feeding screw (36) connected to a rotating shaft of the DC motor (31);
   a supporting member (35) engaged with the feeding screw (36) to be moved back and forth along the feeding screw (36) by rotation of the feeding screw (36);
   an injection piston (45) coupled to the supporting member (35) to be linearly moved together with the supporting member (35);

an injection cylinder (46) supported by two fixing plates (37 and 39) and receiving the injection piston (45), the injection cylinder (46) being provided with a feeding valve (43) adapted to be opened at the time of retraction of the injection piston (45) and an exhaust valve (44) adapted to be opened at the time of extension of the injection piston (45);

a liquid supplying container (48) connected to the feeding valve (43) of the injection cylinder (46) for supplying liquid for generating plasma to the injection cylinder (46); and a displacement sensor (49) provided at the fixing plate (37) to detect a position of the injection piston (45).

* * * * *